(12) United States Patent
Clarke et al.

(10) Patent No.: US 8,419,684 B2
(45) Date of Patent: Apr. 16, 2013

(54) INTRADERMAL DELIVERY DEVICE

(75) Inventors: Richard P. Clarke, Raleigh, NC (US);
M. Lehag Haider, Cary, NC (US);
Richard J. Klug, Roxboro, NC (US);
Frank E. Martin, Durham, NC (US)

(73) Assignee: Becton, Dickinson and Company,
Franklin Lakes, NJ (US)

( * ) Notice: Subject to any disclaimer, the term of this patent is extended or adjusted under 35 U.S.C. 154(b) by 0 days.

(21) Appl. No.: 12/955,554

(22) Filed: Nov. 29, 2010

(65) Prior Publication Data

US 2011/0071494 A1    Mar. 24, 2011

Related U.S. Application Data

(62) Division of application No. 11/282,591, filed on Nov. 21, 2005, now Pat. No. 7,842,008.

(51) Int. Cl.
*A61M 5/00* (2006.01)

(52) U.S. Cl.
USPC .......................................................... 604/117

(58) Field of Classification Search .................. 604/46, 604/115–117, 164.01, 164.06, 272, 164.07, 604/164.08, 164.09, 158–163
See application file for complete search history.

(56) References Cited

U.S. PATENT DOCUMENTS

| | | | | |
|---|---|---|---|---|
| 1,934,046 A | * | 11/1933 | Demarchi | 604/115 |
| 5,279,544 A | * | 1/1994 | Gross et al. | 604/20 |
| 5,478,315 A | * | 12/1995 | Brothers et al. | 604/115 |
| 6,656,147 B1 | * | 12/2003 | Gertsek et al. | 604/28 |
| 6,808,506 B2 | * | 10/2004 | Lastovich et al. | 604/47 |

* cited by examiner

*Primary Examiner* — Nicholas Lucchesi
*Assistant Examiner* — Leah Stohr
(74) *Attorney, Agent, or Firm* — Roylance, Abrams, Berdo and Goodman, LLP

(57) ABSTRACT

A system and method is provided for an injectable substance delivery device comprising a limiter, shoulder or post, that controls how deep the needle is inserted into the tissue. The limiter is sized in proportions that control the maximum insertion depth of the needle into the tissue without excessively restricting the complete insertion of the needle. The system and method further comprises an normalization or stabilizer ring that prevents distortion of the tissue in the vicinity of the infusion, so that the needle length is the major determining factor as to how deep the infusion is delivered.

15 Claims, 8 Drawing Sheets

INTRADERMAL DELIVERY DEVICE

CROSS-REFERENCE TO RELATED APPLICATIONS

This application is a Divisional application of U.S. Ser. No. 11/282,591, filed Nov. 21, 2005 now U.S. Pat. No. 7,842,008. This application includes subject matter related to that of U.S. Pat. No. 6,537,242, to Phyllis Palmer, entitled "Method And Apparatus For Enhancing Penetration Of A Member For The Intradermal Sampling Or Administration Of A Substance", issued Mar. 25, 2003, and in U.S. patent application Ser. No. 10/238,958, filed on Sep. 11, 2002 by Ronald Pettis et al., entitled "Microneedle-Based Pen Device For Drug Delivery And Method For Using Same", the entire contents of each being incorporated herein by reference.

BACKGROUND OF THE INVENTION

1. Field of the Invention

The present invention relates generally to substance delivery devices. Specifically, the invention relates to an injection device and method that incorporates microneedles and skin tensioning systems for providing an optimal interface for an injection.

2. Description of the Related Art

Currently, various devices have been proposed for monitoring, sampling and delivering substances transdermally. Although the prior subcutaneous delivery methods using a needle for delivering pharmaceutical agents and drugs are effective for many applications, the pain normally induced by the needle has prompted the development of less painful delivery methods. Transdermal delivery is one method of avoiding the pain caused by subcutaneous sampling and delivery using a needle.

In recent years there has been an increased interest in microneedles for sampling and for the transdermal delivery of drugs and other substances. Microneedles are short (generally 3 mm or less) needles that can pierce the skin to a depth wherein a substance can be delivered into the epidermis, such that the substance can be readily absorbed by the body. An advantage of the use of microneedles is their ability to penetrate the outermost layers of the skin with only minor discomfort to the patient, as compared to a standard needle.

As known to those skilled in the art, the skin is made up of several layers, with the upper composite layer being the epithelial layer. The outermost layer of the skin is the stratum corneum, which has well known barrier properties to prevent molecules and various substances, including most pharmaceutical agents, from entering the body, and further preventing analytes from exiting the body. The stratum corneum is a complex structure of compacted keratinized cell remnants having a thickness of about 10-30 microns.

Various methods of delivering drugs through the skin typically form micropores or cuts through the stratum corneum. By penetrating the stratum corneum and delivering the drug to the skin in or below the stratum corneum, many drugs can be effectively administered. The devices for penetrating the stratum corneum generally include a plurality of microneedles or blades having a length to penetrate the stratum corneum without passing completely through the epidermis. Examples of these devices are disclosed in U.S. Pat. No. 5,879,326 to Godshall et al., in U.S. Pat. No. 5,250,023 to Lee et al., and in WO 97/48440, the entire contents of each being incorporated herein by reference.

Accordingly, microneedles have been used with some success for various substances that are effective when delivered transdermally or intradermally. However, many of the prior microneedle devices that are currently available are not able to penetrate the skin uniformly across the microneedle surface, thereby reducing the surface area available for delivery of the substance. That is, skin is generally elastic and the skin often deforms before the microneedles penetrate. In some instances, the microneedles deform the skin but do not penetrate the skin to a depth sufficient to deliver a drug.

For example, some current microneedle devices are rigid holders that retain a microneedle in the skin by an adhesive or tape on an area of the device some distance from the needle. These devices poorly compensate for the topography of the skin and may not precisely insert the needle the proper distance.

Numerous other methods and devices have been proposed to enhance the permeability of the skin and to increase the diffusion of various drugs through the skin so that the drugs can be utilized by the body. Typically, the delivery of drugs through the skin is enhanced by either increasing the permeability of the skin, or increasing the force or energy used to direct the drug through the skin.

Yet another proposed solution to the above problems is disclosed in U.S. Pat. No. 6,808,506 to Lastovich et al., the entire contents of which are incorporated herein by reference. The Lastovich patent discloses an apparatus for delivering or withdrawing a substance through at least one layer of the skin. For example, the Lastovich patent discloses a device to deliver a substance to one or two different depths, and specifically, to two different physiological tissue compartments, such as shallow subcutaneous and intradermal. As the skin of a subject has elastic properties that resist penetration by the dermal-access members, the skin can be stretched by a raised first surface area of the device until the skin is taut before the dermal-access members of the device penetrate the skin. A penetrating pressure can then be applied to the device until a first surface area contacts the skin. This promotes uniform penetration of the skin by each of the dermal-access members.

These prior methods and apparatus for the transdermal administration of drugs, however, have exhibited limited success especially in regard to leakage rates. Accordingly, a continuing need exists in the industry for an improved device for delivering substances with minimal leakage rates.

SUMMARY OF THE INVENTION

An object of the present invention is to provide an injection device that incorporates microneedle and skin tensioning systems to form an optimal interface for injection.

Another object of the present invention is to provide an injection device that delivers a substance to a targeted region of the skin with minimal leakage.

Another object of the present invention is to provide an injection device that delivers a substance to a targeted region of the skin with minimal leakage by using a skin tensioning system comprising a coordinated use of a limiter that controls how deep a needle is inserted into the tissue, and a stabilizer ring that prevents distortion of the tissue in the vicinity of the infusion so that needle length is the major determining factor as to how deep the infusion is delivered.

Another object of the present invention is to provide an injection device that delivers a substance to a targeted region of the skin with minimal leakage by using a flexible needle holder to fully conform to the dermis layer.

Another object of the present invention is to provide the flexible needle holder with a spring-loaded depressor for pushing against the needle during initial insertion.

Another object of the present invention is to provide an injection device that delivers a substance to a targeted region of the skin with minimal leakage by using a needle holder for reducing site pressure at the area of needle injection by providing an air space or a vacuum space about the needle holder.

Another object of the present invention is to provide an injection device that delivers a substance to a targeted region of the skin with minimal leakage by using a needle holder for reducing site pressure at the area of needle injection by providing a free-floating needle holder or an inclined needle holder.

These and other objects are substantially achieved by providing a system and method for a substance delivery device which includes a number of aspects to minimize the deformation of the skin surface during an injection, and which delivers a substance to a targeted region of the skin with minimal leakage. The system and method comprises a limiter, shoulder, or post, that controls the depth of insertion of the needle into the tissue. The limiter is sized in proportions that control the maximum insertion depth of the needle into tissue without excessively restricting the complete insertion of the needle. The system and method further comprises a normalization or stabilizer ring that prevents distortion of the tissue in the vicinity of the insertion site, so that needle length is the major determining factor as to how deep the substance is delivered.

In the embodiment of the present invention, a correlation can exist between the size of the stabilizer ring and the amount of substance to be injected, and between a height of the limiter and a height of the stabilizer ring.

These and other objects are also substantially achieved by providing a system and method for a substance delivery device which includes a flexible needle holder such that the injection device conforms with the dermis, or further provides an air-space about the needle at the insertion site, and which delivers a substance to a targeted region of the skin with minimal leakage. In this method, the area around the needle insertion site is not contacted by the supporting device.

Further objectives and advantages, as well as the structure and function of exemplary embodiments, will become apparent from a consideration of the following description, drawings and examples.

BRIEF DESCRIPTION OF THE DRAWINGS

These and other objects, advantages and novel features of the present invention will be more readily appreciated from the following detailed description when read in conjunction with the accompanying drawings, in which.

In the drawing figures, it will be understood that like numerals refer to like elements, features and structures.

DETAILED DESCRIPTION OF EXEMPLARY EMBODIMENTS

Figure 2:
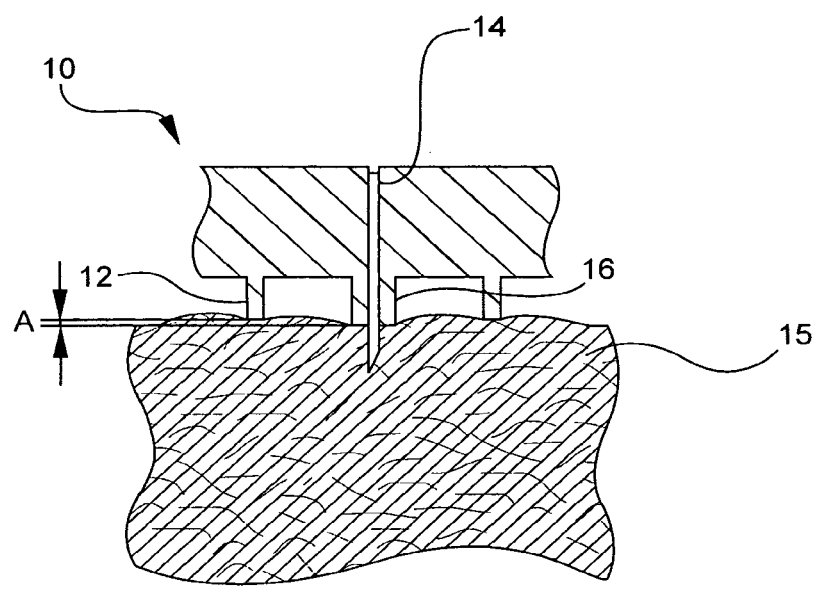
FIG. 2 is an enlarged cross sectional view of a skin tensioning system having a limiter and stabilizer ring in accordance with an embodiment of the present invention.

For delivery devices, various microneedle systems can be incorporated to function both as the drug outlet and the biological interface with the patient or end-user. In the exemplary embodiments of the present invention described below, the microneedle device includes a single or multineedle-array needle head or hub assembly that can be integral with an injection device or used as a simple attachment, and is adaptable to a variety of currently manufactured devices.

Exemplary embodiments of the present invention incorporate a limiter and ring configuration in which each needle of the assembly protrudes from a limiting member, such as a post, surrounded by a valley or gap, and is then circumscribed by an additional skin tensioning member, such as a ring of a height and diameter relative to the limiter. This arrangement assists in skin tensioning, limits needle penetration, and allows an area for formation of the intradermal bleb or wheal during injection such that injection leakage is minimized.

A diagram of an exemplary head or hub assembly 10 in accordance with an embodiment of the present invention is shown in FIG. 1. FIG. 1 is a perspective view of a drug outlet and biological interface for use with a microneedle system in accordance with an embodiment of the present invention. Specifically, the exemplary drug outlet and biological interface, or hub assembly 10 comprises a limiter and ring configuration in which each needle of the assembly protrudes from a limiting member, such as a post 16, surrounded by a valley or gap, and is then circumscribed by an additional skin tensioning member, such as a ring 12 of a height and diameter relative to the limiter. An attachment mechanism 18, such as a grooved snap-fit mechanism, can further be provided for securing the hub assembly 10 to a delivery device. As noted above, when used with a delivery device, this arrangement assists in skin tensioning, limits needle penetration, and allows an area for formation of the intradermal bleb or wheal during injection such that injection leakage is minimized A detailed description of exemplary embodiments will now be provided with reference to FIGS. 2, 3 and 4.

For the following discussion, reference will be made to FIGS. 2, 3, and 4, and as necessary, attention will be drawn to a particular drawing figure. FIG. 2 is an enlarged cross sectional view of a skin tensioning system having a limiter and stabilizer ring in accordance with an embodiment of the present invention. FIG. 4 is another enlarged cross sectional view of a skin tensioning system having a limiter and stabilizer ring in accordance with an embodiment of the present invention, and FIG. 5 is an enlarged cross sectional view of a limiter for illustrating skin deflection.

Figure 3:
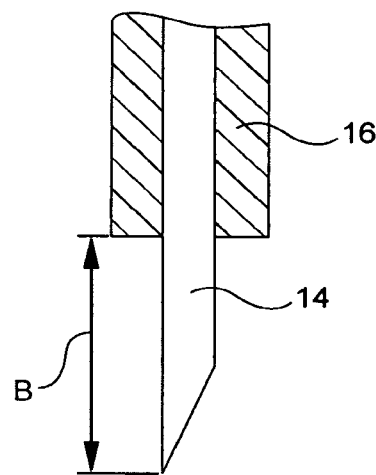
FIG. 3 is an enlarged cross sectional view of an exemplary limiter of FIG. 2.
Figure 4:
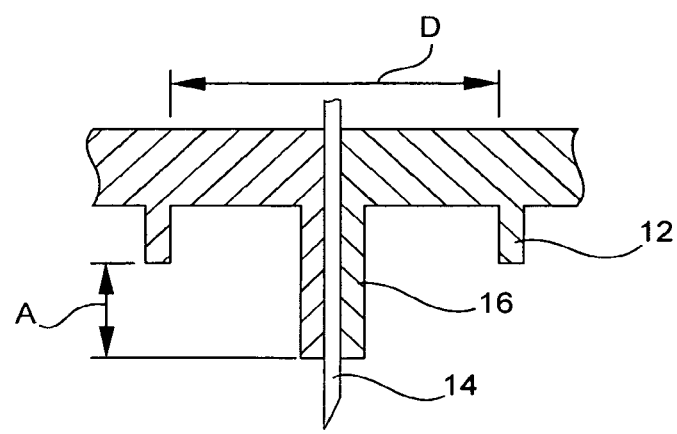
FIG. 4 is an enlarged cross sectional view of a skin tensioning system having a limiter and stabilizer ring in accordance with an embodiment of the present invention.
Figure 5:
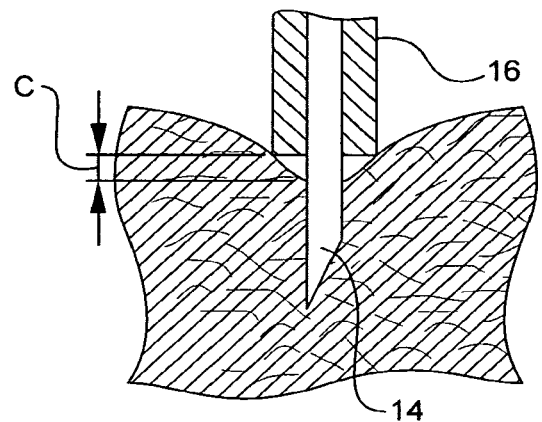
FIG. 5 is an enlarged cross sectional view of a limiter for illustrating skin deflection.

FIGS. 2, 3, and 4 illustrate an exemplary head or hub assembly 10 in accordance with an embodiment of the present invention. The hub assembly 10 includes a stabilizer ring 12, at least one microneedle 14 shown penetrating a skin surface 15, and a limiter 16. The hub assembly 10 is disposed at a proximal end of a device (not shown), and provides the microneedle 14 extending in an axial direction from the limiter 16. The hub assembly 10 also provides the stabilizer ring 12 extending in the axial direction and being concentrically disposed about the microneedle 14 and the limiter 16. As shown in FIG. 4, the limiter 16 extends in the axial direction beyond the stabilizer ring 12 by a distance "A". Also, as shown in FIG. 3, the microneedle 14 extends in the axial direction beyond the limiter 16 by a distance "B".

The hub assembly 10, stabilizer ring 12, and limiter 16 can be constructed of any suitable material that is compatible with the contents being delivered. This includes injection molded polymers, polycarbonate, COC polymer, and similar materials that are inexpensive and easy to mold and manufacture. The microneedle 14 can also be constructed of any suitable material, but is preferably constructed of steel.

In FIG. 2, when the head or hub assembly 10 makes contact with a patient surface 15, such as skin, the skin tensioning normalization or stabilizer ring 12 contacts the surface shortly after the microneedle 14 begins to deform the surface prior to penetration. The stabilizer ring 12 minimizes deformation of the surface 15, allowing greater accuracy in microneedle 14 penetration. The skin surface 15 contacts the shoulder or post of the limiter 16, which limits insertion depth. As shown in FIG. 5, microneedle insertion where a tensioning member is lacking results in greater deformation and thinning of the skin surface 15, creating poor microneedle insertion and inaccurate tissue depth targeting.

The embodiments of FIGS. 2 and 4 minimize the deformation of the skin surface 15 during an injection, and improve infusion through the needle 14 into the intradermal and shallow subcutaneous tissue to minimize leakage. These embodiments comprise at least two parts.

A first part comprises the limiter 16, having a shoulder or post that controls the depth of insertion of the needle 14 into the tissue. The limiter 16 is dimensioned to control the maximum insertion depth of the needle 14 into tissue without excessively restricting the complete insertion of the needle.

A second part comprises the normalization or stabilizer ring 12 that prevents distortion of the tissue in the vicinity of the infusion, so that needle length is the major determining factor as to how deep the infusion is delivered. In the example shown in FIGS. 2 and 4, the stabilizer ring 12 is provided in the form of a continuous ring, however, any number of shapes can be used.

In order to limit the depth of penetration of the needle 14, the limiter 16 is preferably incorporated into an intradermal (ID) needle device. Such a limiter 16 can be constructed as a shoulder on the needle 14, and has a slightly larger diameter than that of the needle 14.

The limiter 16 prevents the needle 14 from being inserted beyond a certain point. Traditionally, the limiter 16 has been the needle hub or other device part that is of significantly larger diameter than the needle. With microneedles that are short (i.e., 3 mm or less) it becomes important to make the limiter 16 of a sufficiently small diameter to allow the microneedle to fully insert.

When the needle 14 begins to penetrate skin surface 15, the skin surface 15 distorts until the force normal exceeds the needle 14 penetration force. Needle penetration force is dependent on bevel geometry, needle diameter and lubrication. A large limiter 16 diameter can prevent the skin from distorting to the point where the needle 14 will not penetrate completely. That is, the shoulder or limiter 16 affects the amount of the reduced penetration. Accordingly, a smaller limiter 16 diameter can ensure that the needle 14 will more completely penetrate, to the point where the limiter 16 no longer prevents the needle 14 from over penetrating. A limiter 16 with a 90 degree step, and having twice the diameter of the needle 14, is usually sufficient to prevent needle 14 over-penetration.

In an exemplary embodiment as shown in FIG. 3, a needle 14 is shown surrounded by the limiter 16. The limiter 16 can nominally be 2 times the diameter of the needle 14 to optimally control the penetration depth "B". A limiter 16 which is too small (i.e., less than 0.1 times the diameter of the needle 14) may allow further penetration. A limiter 16 which is too large (e.g., 20 times the diameter of the needle 14) may cause surface irregularities to reduce penetration depth. Manufacturing methods may require a limiter 16 diameter to be larger than preferred, however, limiter diameter should preferably be kept to a practical minimum. For example, for a 31 to 34 gauge needle 14, a 0.020 to 0.040 inch diameter limiter 16 is sufficient to limit penetration depth. Accordingly, in an exemplary embodiment of the present invention, a 0.040 inch diameter limiter 16 is preferable to limit penetration depth. Additionally, the body of the limiter 16 between the skin contact surface and the injection device can be provided in a substantially cylindrical or slightly conical shape to simplify manufacturing of the device (for example, to provide desirable mold release), however, any number of suitable body shapes can be used such as square or star shaped limiter. However, a circular limiter 16 is more preferable than a square limiter.

The limiter 16 should preferably extend from the body of the device 10 sufficiently so that the body of the device 10 does not become a defacto limiter. During insertion of the needle 14 into the skin surface 15, the tissue distorts to an angle sufficient to reach the needle penetration force. If this angle causes the tissue to press against the body of the device 10, then the device will become the depth limiter rather than the limiter 16. The ideal limiter 16 extension length will substantially depend on the needle geometry. A sharper needle will result in less tissue distortion and will require less limiter 16 extension to fully seat the needle 14.

As shown in FIG. 4, the limiter 16 extends in the axial direction beyond the stabilizer ring 12 by a distance "A", and the microneedle 14 extends in the axial direction beyond the limiter 16 by a distance "B". A limiter 16 extension length that is the same or somewhat less than the needle 14 length is usually sufficient to seat the needle fully. As noted above, a correlation can exist between a height of the limiter 16 and a height of the stabilizer ring 12. Accordingly, a key factor in the embodiments of the present invention is the extension height relationship between the limiter 16 and the stabilizer ring 12. Accordingly, in a preferred embodiment of the present invention, the limiter 16 extends in the axial direction beyond the stabilizer ring 12 by a distance of +0.040 inch.

By seating the needle 14 completely, an intradermal device 10 will work more reliably with fewer failures due to leakage and better control over the delivery of the infusate to the targeted depth. For example, when using a handheld intradermal (ID) injection device, the device is held against the skin with sufficient force to prevent retraction of the needle from the skin during injection. Due to the small dimensions inherent in an ID needle, this force can distend the tissue by the shoulder width sufficiently to affect the injection by a distortion reduced penetration depth "C", as shown in FIG. 5. FIG. 5 is an example of reduced penetration due to excessive shoulder width. In the absence of the stabilizer ring 12, a user could push the limiter 16 hard enough to thin the skin.

The distension of the tissue can thin the skin locally or compress the skin, thereby allowing the needle 14 to penetrate subcutaneously (SC). The needle tip can also become occluded with tissue. Occlusion of the needle 14 can significantly increase the force that is required to inject the infusate. To minimize the distention/compression of the tissue at the needle insertion point, the stabilizer ring 12 can be employed. As a user hold the device against the skin with a sufficient force to prevent retraction of the needle 14 from the skin during injection, a normalization or stabilizer ring 12 can transfer tissue compression away from the needle 14 site, allowing proper penetration depth as shown in FIG. 2 and minimizing leakage due to improper needle penetration and/or tissue distortion at the injection site.

The stabilizer ring 12 provides a feature for preventing excessive flexure of the tissue surrounding the needle 14. When the needle 14 is inserted into the tissue, a minimum force is required to penetrate the skin surface 15 and seat the needle. This force is dependent on the sharpness of the needle 14 (i.e., bevel geometry, finish and the like) and needle 14 diameter.

Once the minimum penetration force is achieved, any force above that can distort the tissue around the needle 14 and limiter 16. Because intradermal needles are short and easily unseated if a light force is used, a higher force is preferred to prevent such unseating. The higher force can, however, also distort the tissue excessively and result in injections that are difficult to deliver (through high injection force), injections that penetrate too deeply (through tissue compression) or injections that leak (through incision stretch). By adding the stabilizer ring 12 about the limiter 16 of the needle 14, any extra distortion of the tissue can be transferred to a region away from the needle 14.

The stabilizer ring 12 should not be so close to the needle 14 that it will interfere with proper seating of the needle 14, nor should it be so far away from the insertion point that it does not transfer tissue distortion away from the site and minimize leakage at the injection site. Also, as noted above, a correlation can exist between the size of the stabilizer ring and the amount of substance to be injected for the prevention of leaks at the injection site. Accordingly, another key factor in the embodiments of the present invention is the distance relationship between the stabilizer ring 12, the limiter 16, and the amount of substance to be injected. The shape of the stabilizer ring 12 should be sufficient to transfer tissue distortion uniformly around the insertion point as a user holds the device against the skin with a sufficient force to prevent retraction of the needle 14 from the skin during injection. One such shape is a continuous ring shape, as illustrated in the exemplary embodiment of the injection system shown in FIG. 1. However, in yet other embodiments of the present invention, the stabilizer ring 12 can be configured as any suitable continuous or noncontinous shape to surround the limiter 16 which is capable of transferring tissue distortion uniformly around the insertion point.

As noted above, the stabilizer ring 12 should have sufficient clearance from the limiter 16 to avoid interference with skin irregularities, and to allow the limiter 16 to control needle 14 depth penetration. As shown in the exemplary embodiment of FIG. 4, the shoulder of the limiter 16 should preferably extend a distance "A" slightly beyond the stabilizer ring 12 (that is, in the direction of the needle tip) by a distance of about 0.020 to about 0.100 inches, with an extension of between about 0.020 and about 0.060 inches being most preferred. As shown in FIG. 4, the stabilizer ring 12 should preferably have an inner diameter "D" of between about 0.100 to about 1.00 inches, with an inner diameter of between about 0.250 and about 0.500 inches being most preferred. As noted above, in the embodiments of the present invention a correlation can exist between the inner diameter of the stabilizer ring and the amount of substance to be injected. For example, for a large injection (for example, 0.25 to 0.50 cc), the inner diameter "D" of the stabilizer ring 12 should be near the maximum value of 1.00 inches. For a small injection (for example, 50 to 100 microliters), the inner diameter "D" of the stabilizer ring 12 should be near the minimum value of 0.10 inches. Accordingly, in an exemplary embodiment of the present invention, a stabilizer ring 12 inner diameter "D" of about 0.250 inches is preferable. In such a configuration, the distance provided between the inner diameter of the stabilizer ring 12 and the limiter 16 is larger than the diameter of the limiter 16. For example, in the exemplary embodiment shown in FIG. 1, the stabilizer ring 12 extends around the outer circumference of the hub assembly 10 (that is, at a maximum inner diameter D), but is not limited thereto. In the exemplary embodiment shown in FIG. 2, the stabilizer ring 12 extends at a distance less than the outer circumference of the hub assembly 10 (that is, at an inner diameter D less than maximum). The stabilizer ring 12 can be comprised of any suitable material, but is preferably comprised of a rigid material such that the stabilizer ring 12 is not deflected by contact with the skin surface.

The function of the stabilizer ring 12 is to allow the expansion of the wheal and prevent compression or distortion of tissue in the vicinity of the injection site. To achieve this, the stabilizer ring 12 contacts the skin surface shortly after the microneedle 14 begins to deform the skin surface 15. Specifically, the needle 14 first contacts the skin surface 15. This results in a tissue deflection and an angle is formed defining the degree of skin deflection. At this point, the needle 14 penetrates the skin surface 15 and generally maintains the degree of skin deflection created earlier. The angle defining the degree of skin deflection is maintained until the skin surface 15 contacts the limiter 16. At this point, the stabilizer ring 12 contacts the skin surface 15 to thereby move a larger volume of tissue and allow the user to push the device even harder against the skin surface without going subcutaneous or displacing the needle 14. That is, through the contact with the skin surface 15, the stabilizer ring 12 transfers tissue compression away from the needle 14 site allowing proper penetration depth and preventing tissue distortion to minimize leakage at the injection site. Accordingly, the inner diameter "D" of the stabilizer ring 12 should be large enough to allow expansion of the wheal, but not too large as to become ineffective at preventing compression of tissue.

Another factor regarding proper injection is needle configuration. Needles that utilize a short bevel may not fully penetrate the skin due to local distension or distortion of the tissue. Unless the needle is infinitely sharp (i.e., zero penetration force required), some tissue distortion will occur as shown in FIG. 5. As described in greater detail below, needle sharpness (i.e., bevel) should be optimized, to reduce distortion.

Using a minimal diameter limiter 16 will also minimize reduced penetration depth due to tissue distortion. At the same time, the limiter 16 diameter should be large enough to prevent the limiter 16 from following the needle 14 into the skin surface 15, and the needle bevel should be short enough to deliver the infusate into the dermis without leaking onto the skin surface or excessively into the subcutaneous (SC) tissue.

Accordingly, in an exemplary embodiment of the present invention incorporating each of the above features, a short needle 14 is set in a cylindrical or conical mount or limiter 16 with a circular stabilizer ring 12. The limiter 16 is preferably about 0.040 inches in diameter at the tip, which acts as a sufficient limiter. The stabilizer ring 12 preferably has a 0.25 inch inner diameter (ID). The limiter 16 preferably extends about 0.040 inches beyond the plane of the stabilizer ring 12 as shown in FIG. 4. The sharper the needle 14, the less extension is required. Sharper needles, however, typically have a longer bevel length, which can require deeper insertion into the tissue to prevent leakage. With very long bevels, it becomes difficult or impossible to deliver intradermally without leakage.

Figure 1:
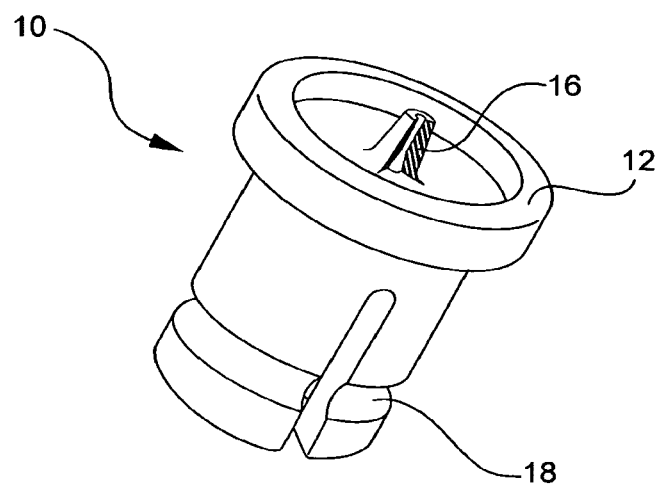
FIG. 1 is a perspective view of a drug outlet and biological interface for use with a microneedle system in accordance with an embodiment of the present invention.

Uses for the embodiments of the present invention can include, but are not limited to, a syringe, an autoinjector, or a pen needle. When used on a syringe, embodiments of the present invention can be integrated as part of the glass syringe tip of a unitized syringe, or molded into the end of a plastic syringe. Embodiments of the present invention can also be provided as a separate piece as shown in FIG. 1, such as a luer adapter that slips on or is threaded onto the end of a glass or plastic syringe. Other methods may also be used to attach embodiments of the present invention as separate adapters to a syringe, such as a snap-on attachment, gluing, sonically welding, or other standard manufacturing methods.

A separate adapter can be one or multiple pieces that incorporate the needle 14, the limiter 16 and/or the stabilizer ring 12, and can interface with the drug delivery device. Embodiments of the present invention can also be part of an autoinjector, such as an autoinjecting syringe. A detachable needle such as that used in pen-type injectors (e.g., insulin pens) can also benefit from the embodiments of the present invention. Additionally, any device that is designed to deliver a shallow (i.e., less than or equal to 4 mm) injection can benefit from the embodiments of present invention.

A limiter 16 and stabilizer ring 12 can offer significant advantages over current intradermal delivery systems. The limiter 16 can provide much better control over exactly how deeply a needle 14 is inserted as compared to larger limiters without extensions. More precise delivery to the targeted tissue depth with less leakage is the result. The stabilizer ring 12 can improve performance as compared to current designs without a stabilizer ring for substantially the same reasons, in addition to compensating for variable application forces applied by the user.

In tests, a stabilizer ring 12 with a +0.040 inch limiter 16 protrusion (that is, the protrusion "A" of the limiter 16 beyond the stabilizer ring 12), a stabilizer ring with a +0.020 inch limiter protrusion, a stabilizer ring with a −0.020 inch limiter protrusion (i.e., recessed 0.020 inches), and a device having a limiter but no stabilizer ring, each having a 1.5 mm, 31 gauge needle with a 28 degree bevel, were compared over a number of injections. A control device was also provided having a 1.5 mm, 30 gauge needle, with a 3-angle bevel controlled by a 5.5 mm limiter cap.

The tests showed that the devices with the longest limiter 16 projection beyond the stabilizer ring 12 performed best. This could include devices having a 0.040 inch and larger limiter protrusion. Specifically, in a number of first tests, the tests showed that the device having a stabilizer ring with a 0.040 inch limiter protrusion was preferable, as it consistently gave ID injections without leakage.

The first tests further showed that the device with a stabilizer ring 12 with a 0.020 inch limiter 16 protrusion had a number of injections which leaked relative to the device with a stabilizer ring with a 0.040 inch limiter protrusion. The device with a stabilizer ring 12 with a −0.020 inch limiter 16 protrusion (i.e., recessed 0.020 inches), leaked in an even larger number of injections. The device having no stabilizer ring 12 did not leak in most injections, however, the injections lacked a blanched wheal indicating that the injections appeared to become subcutaneous (SC). In contrast, the injections of the device with a stabilizer ring 12 with a 0.040 inch limiter 16 protrusion each had a well-defined blanched wheal indicating proper ID delivery. The control device was relatively leak free but the depth of delivery was difficult to control, and often became SC. A result comparison of various devices is illustrated in the graph of FIG. 17.

Figure 17:
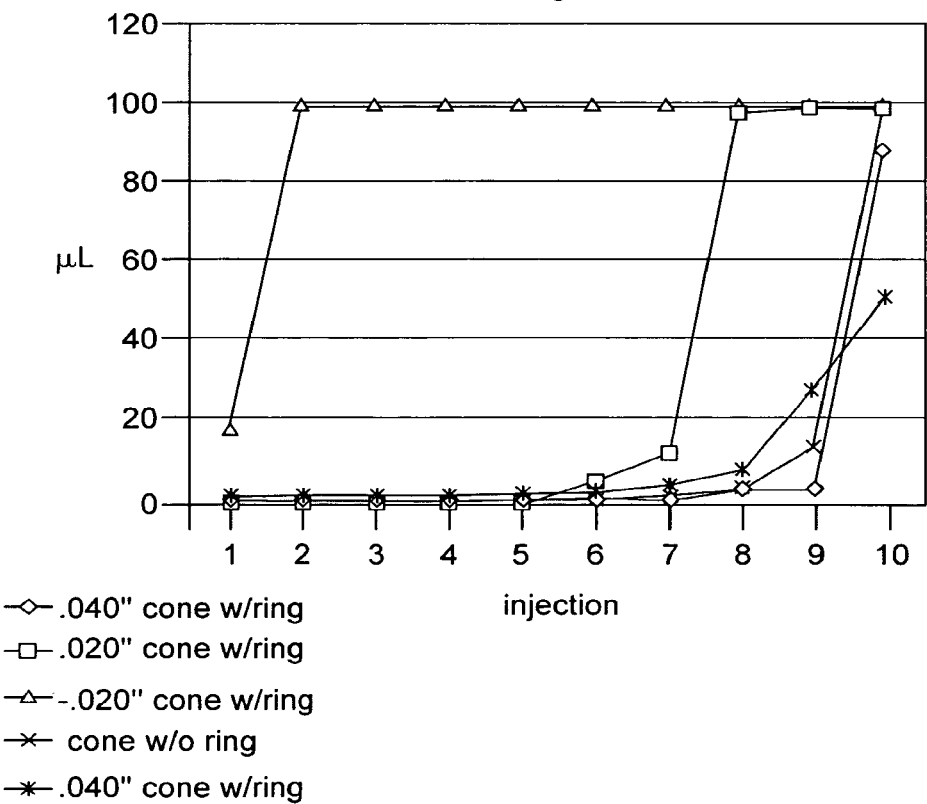
FIG. 17 is a graph illustrating a comparison of leakage values.

FIG. 17 is a graph illustrating a comparison of leakage values for five devices. The graph illustrates that over a test comprising ten injections, the device having a stabilizer ring 12 with a 0.040 inch limiter 16 protrusion was preferable when leakage was measured.

The proper ID delivery of the device with a stabilizer ring 12 with a 0.040 inch limiter 16 protrusion can be due, in part, to the use of a 28 degree bevel on the needle, however, this bevel may be less capable of penetration than a 3-angle bevel. Another factor is variations in actual needle lengths, as longer needles are more likely to inject SC. Still another factor is the degree of skin compression. For example, in the device having no stabilizer ring 12, injection leaks may result from the compression of the tissue to the point where the dermis thinned significantly, allowing the needle to extend further than in devices with broader footprints.

As noted above, the devices with the longest limiter 16 projection beyond the stabilizer ring 12 performed best. This could include devices having a 0.060 inch, 0.080 inch, and 0.10 inch limiter 16 protrusion. Accordingly, in tests of such additional embodiments, the following results were obtained.

In a number of second tests, a stabilizer ring 12 with a 0.030 inch limiter 16 protrusion (device 1), a stabilizer ring with a 0.040 inch limiter protrusion (device 2), and a stabilizer ring with a 0.060 inch limiter protrusion (device 3), each having a 1.5 mm, 31 gauge needle with a 3-angle, 0.48 mm bevel length, were compared over a number of injections.

The second tests showed that these devices were less leak-prone and injected deeper. The device with a stabilizer ring 12 with a 0.040 inch limiter 16 protrusion had much less blanching, due in part to the needle type used. The 3-angle bevel is sharper and better at penetrating, and becomes SC more often. The limiter 16 length extending beyond the stabilizer ring 12 also showed an effect on the blanching. The longer the limiter 16 length extending beyond the stabilizer ring 12, the fewer blanched wheals were produced. This could also be due to better needle penetration.

Where there was no normalizing or stabilizer ring 12, deep ID injections were achieved. The effort required for injection was also higher, since without the stabilizer ring 12, there was more compression of tissue local to the needle.

As shown in Table 1 below, blanching (i.e., shallow ID injection) is more likely to occur with devices 1 and 2 using shorter limiters 16 (i.e., 0.030 inch and 0.040 inch). Accordingly, a preferred embodiment would provide a small diameter limiter 16 to control the depth of penetration of the needle 14, and a stabilizer ring 12 that prevents over-compression of the tissue. The preferred height of the limiter 16 past the stabilizer ring 12 is substantially dependent upon the needle sharpness.

TABLE 1

| Device Number | Number of injections having leaks of >10% | Injections having wheal present | Injections having blanching present |
|---|---|---|---|
| 1 | 0 | 15 | 12 |
| 2 | 0 | 15 | 8 |
| 3 | 0 | 15 | 1 |

For example, in non-human tests a preferred embodiment includes a single angle 28 degree, EDM bevel, 31 gauge needle 14, and at least a 0.040 inch limiter 16 extension beyond the stabilizer ring 12 having an ID of 0.25 inches. This configuration satisfies the first factor, that is the extension height of the limiter 16 beyond the stabilizer ring 12, and satisfies the second factor, that is the distance between the stabilizer ring 12 and the limiter 16, to minimize leakage at the injection site.

A 3-angle bevel, 31 gauge (i.e., 0.48 mm bevel) ID needle 14 works better with a 0.040 inch or shorter limiter 16 extension. The inner diameter "D" of the stabilizer ring 12 is large enough to allow expansion of the wheal, but not too large as to become ineffective at preventing compression of tissue.

Accordingly, the ID needle 14 should be used such that the injection is delivered at the target depth with little or no leakage. As noted above, the dermis is a layer of tissue roughly 2 mm thick, therefore, a needle 14 that penetrates less than 2 mm is preferred. Needle lengths that penetrate 0.5 to 1.5 mm are most preferred. Needle lengths that penetrate less than 0.5 mm can leak depending on gauge, and needle lengths that penetrate more than 1.5 mm can often deliver subcutaneously (SC).

Steel needle gauges of 31 to 34 gauge with short bevels are preferred. Larger diameter needles (i.e., greater than 30 gauge) require an excessive bevel length, making the needle prone to leakage and/or SC delivery. Bevel lengths of less than or equal to 0.75 mm allows the dermis to be targeted without leakage or SC penetration. However, placing a bevel of 0.75 mm or less on a 30 gauge needle or larger diameter needle, yields a needle of insufficient sharpness to obtain reliable penetration. However, steel 31 gauge needles can use a relatively shorter bevel and still penetrate the dermis. A steel 34 gauge needle can have a relatively shorter bevel still, and also produce good penetration.

Bevel geometry and limiter 16 size can affect the reliability of embodiments of the device. An EDM single angle 28 degree bevel on a steel 34 gauge needle produces a bevel length of about 0.33 mm. A steel needle is preferable as other needle materials are typically unable to produce a sufficiently sharp needle having the desired characteristics. Such a 34 gauge needle is sufficiently sharp to penetrate the skin, and is short enough to target the ID space. The same EDM single angle 28 degree bevel on a 31 gauge needle is about 0.5 mm in length. Penetration force is higher and the targeted space is broader, now including about one third of the dermis. However, a ground 3-angle bevel reduces penetration force and maintains a bevel length of about 0.5 mm on a steel 31 gauge needle. A longer bevel on a 31 gauge needle produces a sharper needle, such as a needle with a bevel length of 0.74 mm. This 0.74 mm bevel length is still shorter than a typical IV bevel. A 0.5 mm to 0.75 mm bevel length is the preferred range for ID delivery when using a 31 gauge needle. Accordingly, in an exemplary embodiment of the present invention, an EDM single angle 28 degree bevel on a steel 34 gauge needle is preferable. In yet another embodiment of the present invention, a ground 3-angle bevel on a steel 31 gauge needle can be used.

Figure 6:
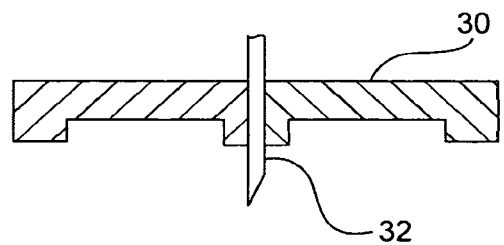
FIG. 6 is an enlarged cross sectional view of a rigid holder.
Figure 7:
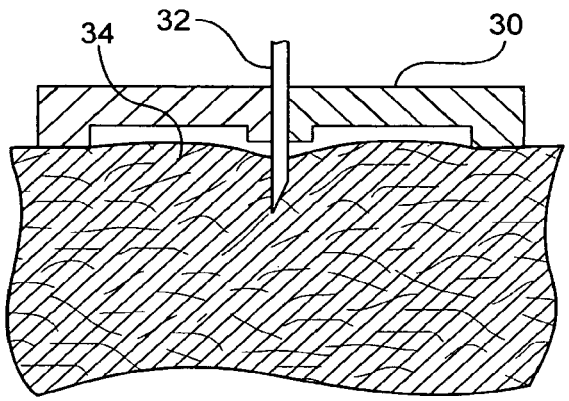
FIG. 7 is an enlarged cross sectional view of the rigid holder of FIG. 6 illustrating poor needle insertion.
Figure 8:
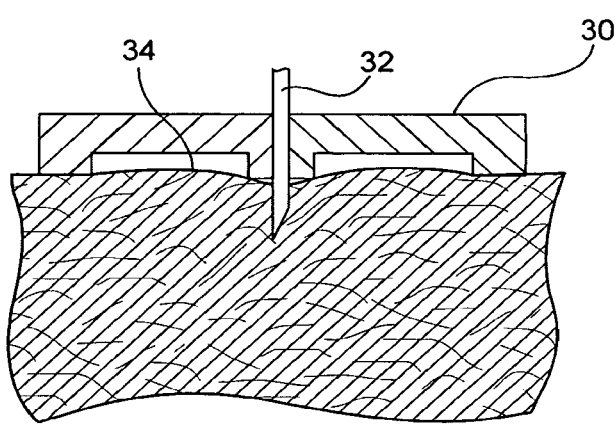
FIG. 8 is an enlarged cross sectional view of the rigid holder of FIG. 6 illustrating minimum preload.

Also, as noted above, current devices poorly compensate for the topography of the skin and may not precisely insert the needle the proper distance as shown in FIGS. 6, 7, and 8. FIG. 6 is an enlarged cross sectional view of a rigid holder, FIG. 7 is an enlarged cross sectional view of the rigid holder of FIG. 6 illustrating poor needle insertion, and FIG. 8 is an enlarged cross sectional view of the rigid holder of FIG. 6 illustrating minimum preload. In this example, the rigid holder 30 disposed about the needle 32 in the device of FIG. 6 does not conform to the skin surface 34 during use and results in poor injection performance.

This can be improved by preloading the needle slightly with one or more spring members as shown in FIGS. 9, 10, 11, and 12. The needle 56 is allowed to float and move with the skin surface 54 without exerting an excessive force against the skin surface. With the flexible holder as shown in FIGS. 9, 10, 11, and 12, the holder and needle conform with the dermis.

Figure 9:
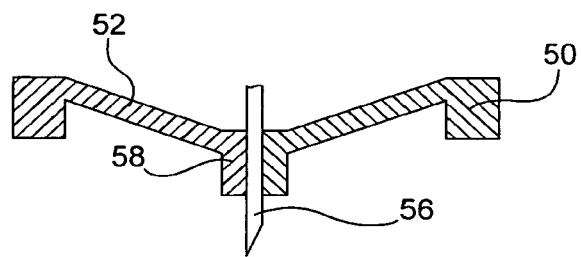
FIG. 9 is an enlarged cross sectional view of a flexible holder in accordance with an embodiment of the present invention.
Figure 10:
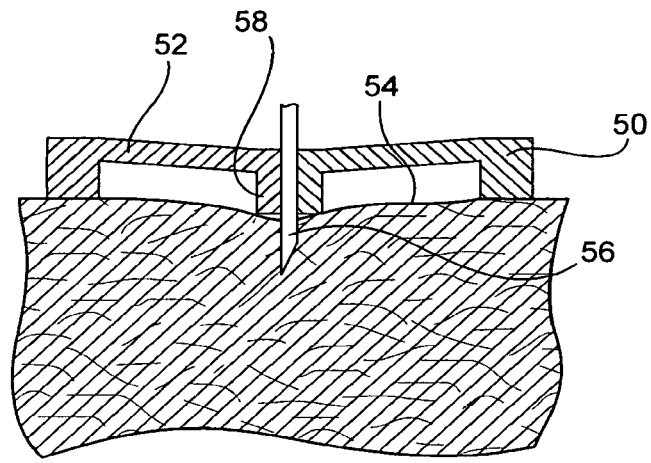
FIG. 10 is an enlarged cross sectional view of the flexible holder of FIG. 9 in a first conforming position.
Figure 11:
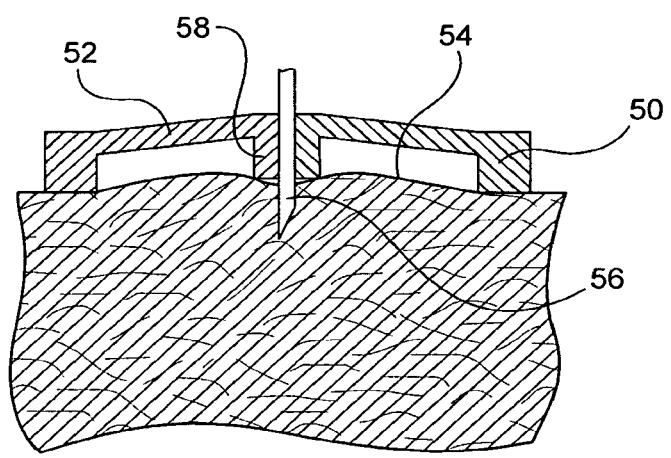
FIG. 11 is an enlarged cross sectional view of the flexible holder of FIG. 9 in a second conforming position.

FIG. 9 is an enlarged cross sectional view of a flexible holder 50 in accordance with an embodiment of the present invention, and FIGS. 10 and 11 are enlarged cross sectional views of the flexible holder of FIG. 9 in a first and second conforming position. The flexible holder 50 comprises a spring member 52 to support the needle 56 and the limiter 58, and can be disposed at a proximal end of a device substantially as described above. As shown in a pre-use position in FIG. 9, the spring member 52 can preload the needle 56 slightly in the proximal direction. Accordingly, during use as shown in FIGS. 10 and 11, the flexible holder 50 can more easily conform with the skin surface 54 to ensure proper injection.

Figure 12:
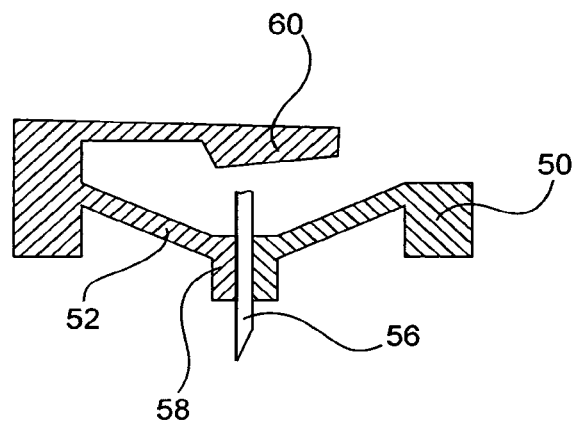
FIG. 12 is an enlarged cross sectional view of a flexible holder further including a spring-loaded depressor in accordance with an embodiment of the present invention.

FIG. 12 is an enlarged cross sectional view of a flexible holder 50 further including an integral spring-loaded depressor 60 in accordance with an embodiment of the present invention. The depressor 60 is added to ensure that the needle 56 can be inserted fully on initial application. The depressor 60 is a momentary contact type, and does not normally press against the needle holder.

Other methods of skin tensioning can be incorporated as an alternative to the stabilizer ring and post limiter system described above. Such methods of skin tensioning can include transiently applying a brief initial vacuum to the injection site, manually or mechanically pulling or stretching the skin, or utilizing a mechanically controlled rapid insertion. For example, ballistic inserters result in brief inertial stiffening of the skin, thereby reducing effective elasticity. These mechanisms can be used either singularly or in combination, or with other techniques readily known to those skilled in the art.

Applications of the embodiments of the present invention can further be applicable in infusion devices. However, during ID infusion, applying pressure to the area of the needle insertion site can increase the backpressure of the infusion, that is, the pressure required to inject infusate intradermally. Therefore, reducing or eliminating pressure to the site of infusion also reduces the backpressure required to infuse. Accordingly, still other embodiments of the present invention can be applied to eliminate pressure to the infusion site for infusion applications.

Figure 13:
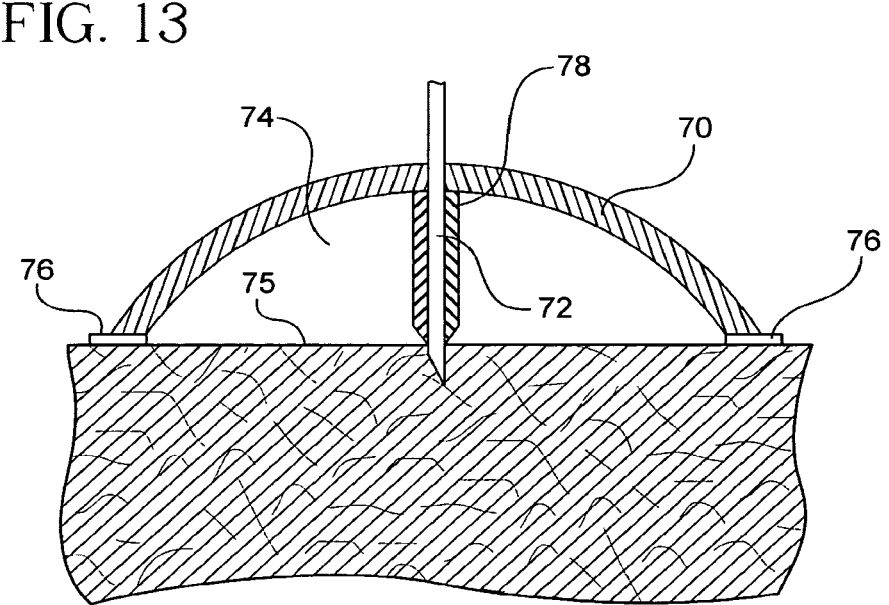
FIG. 13 is an enlarged cross sectional view of an air-space surrounded needle in accordance with an embodiment of the present invention.
Figure 14:
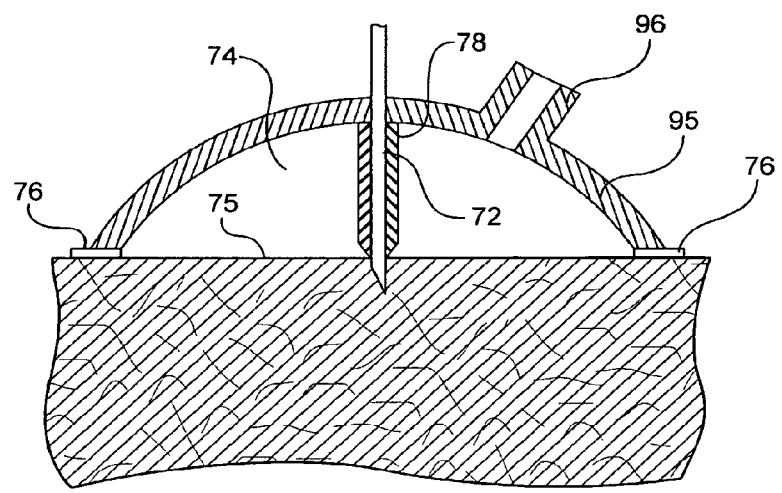
FIG. 14 is an enlarged cross sectional view of a vacuum-space surrounded needle in accordance with an embodiment of the present invention.
Figure 15:
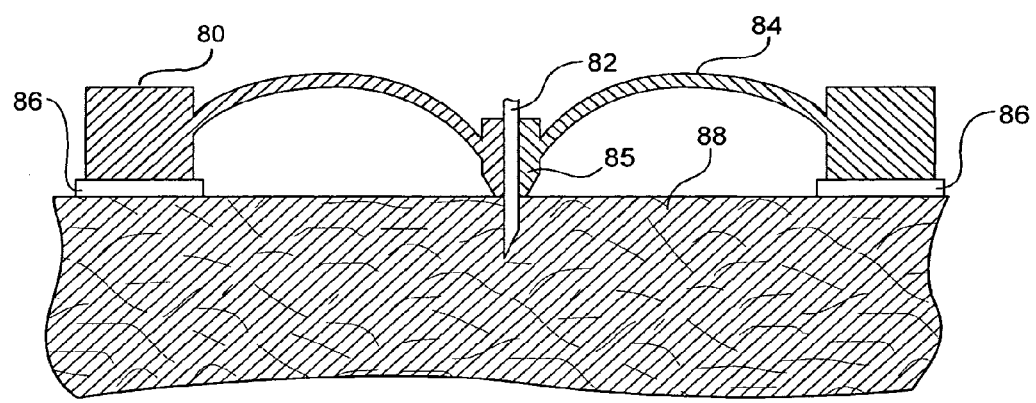
FIG. 15 is an enlarged cross sectional view of a free-floating needle in accordance with an embodiment of the present invention.

A method and apparatus to achieve this is shown in FIGS. 13, 14, and 15. FIG. 13 is an enlarged cross sectional view of an air-space surrounded needle in accordance with an embodiment of the present invention. FIG. 14 is an enlarged cross sectional view of a vacuum surrounded needle in accordance with an embodiment of the present invention, and FIG. 15 is an enlarged cross sectional view of a free-floating needle in accordance with other embodiments of the present invention.

In FIG. 13, the device 70 comprises a needle 72, an air space 74 above a skin surface 75, and an adhesive layer 76, and can be disposed at a proximal end of a device substantially as described above or more preferably, applied as an adhesive attached infusion device. The small gauge needle 72 is shown secured in a limiter 78 and extending from a concave opening at the proximal end of the device 70. The needle 72 extends through the air space 74 and into the skin surface 75. An adhesive layer 76 is disposed at the skin contact surface of the device 70 such that the contact between the concave opening and the skin surface 75 creates the sealable air space 74 therebetween and further ensures that the device 70 is secured to the skin surface 75. In this embodiment of the present invention, the area around the needle 72 insertion site is free of contact by the supporting device 70. In yet another embodiment of the present invention shown in FIG. 14, the device can be accessible to further create a vacuum at the infusion site. The device 95 of FIG. 14 is substantially as described in regard to FIG. 13, with the addition of a vacuum port 96 to the device 95 to allow the creation of a vacuum within the air-space 74. In this embodiment of the present invention, the area around the needle 72 insertion site is also free of contact by the supporting device 95, and the vacuum created further serves to reduce the pressure required for injection or infusion.

In yet another embodiment of the present invention for use in an infusion device, a free-floating needle can be provided to minimize the effect of the device at the insertion site. In FIG. 15, the device 80 comprises a needle 82 and at least one suspender 84, and a limiter 85. An adhesive layer 86 is provided to secure the device 80 to a skin surface 88. In the device 80, the free-floating needle 82 is provided and suspended by the device 80 at a proximal end via the suspender 84. As above, in this embodiment, the area around the needle 82 insertion site is unimpinged by the supporting device 80 as the needle 82 is supported at the insertion site by the limiter 85 and the suspender 84. In doing so, light, flexible movement of the free-floating needle 82 and limiter 85 can be provided. The limiter 85 can be provided substantially as described above, or can be provided in a cone shape as shown in FIG. 15 to further minimize the contact area around the needle 82.

Additionally, in yet other embodiments of the present invention, the supporting device 80 is not required to fully surround the needle 82. For example, the supporting device 80 and suspender 84 can be provided at only one side of the needle 82. As the embodiment of FIG. 15 is preferably not part of a handheld device, but is held in position by adhesive, the supporting device 80 is not required to fully surround the needle 82 to achieve the desired results. Further, the adhesive bond stabilizes and holds the device steady, while the light, flexible movement provided by the suspender 84 prevents unnecessary force and injection pressure, but still allows some force to the tissue to prevent leaks.

Figure 16:
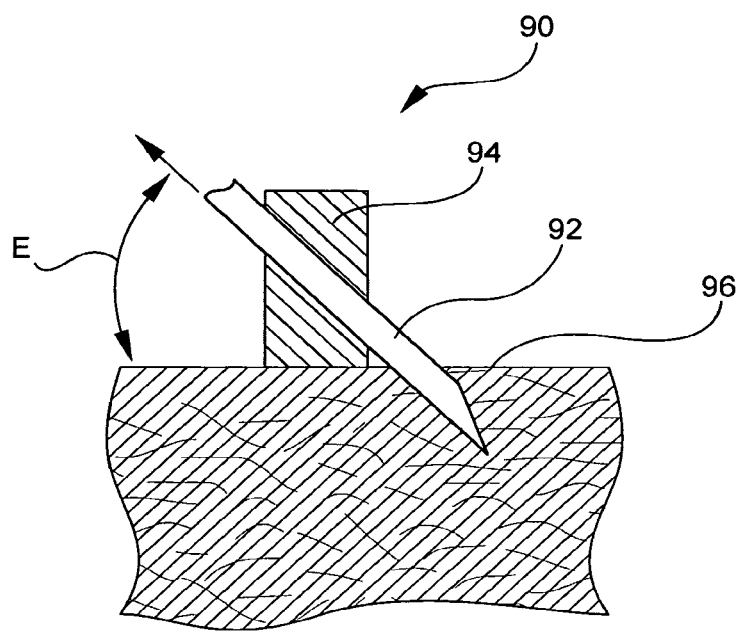
FIG. 16 is an enlarged cross sectional view of an angled needle in accordance with an embodiment of the present invention.

In yet another embodiment of the present invention, the needle positioning can be configured to minimize the effect of the device at the insertion site. In FIG. 16, an angled needle inserter is shown. The device 90 of FIG. 16 includes a needle 92 and a limiter 94. The needle 92 extends from the limiter 94 of the device 90 at an angle "E" (e.g., 30 degrees). In this embodiment, the angle "E" is sufficient to reduce the effects on the insertion site by the injection. Still other embodiments of the present invention can include modified needles to achieve similar results, such as a spring-loaded, needle-in-a-needle.

The embodiments of the present invention described above for a microneedle based system for effective drug delivery to the intradermal or shallow subcutaneous (hypodermis) space, can further include features such as sufficiently open fluid paths to allow ready transport of the liquid or suspension from the device to the microneedles without requiring excessive pressure or occlusion. Also, a biological interface comprised of one or more hollow cannula which can penetrate the stratum corneum can be included, and which can accurately access the desired tissue depth in the skin, and transmit a desired fluid volume through the body of the interface into the specified or targeted tissue space both accurately, with minimal or no fluid loss out of tissue to surface or to untargeted tissue, and efficiently, in a manner that is amenable to the device user and recipient. The delivery system can also serve to reduce pain due to instillation and provides better access to the desired tissue space.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims and equivalents thereof.

What is claimed is:

1. An injectable substance delivery device comprising:
   at least one needle having a length sufficient to penetrate a skin surface of a patient to an intradermal depth for infusing a substance;
   a limiter pre-loaded toward said skin surface for controlling a needle insertion depth, wherein said limiter controls a maximum insertion depth of said needle into said skin surface without restricting complete insertion of said needle; and
   a rigid stabilizer flexibly coupled to said limiter at a first distance from said limiter for allowing an increased application force of said limiter while preventing distortion, compression, or thinning of tissue in a vicinity of a needle insertion site such that said needle length and said limiter determine the depth at which said infusion is delivered, wherein said first distance is determined based upon an amount of said substance to be infused and a diameter of said limiter, and
   wherein said limiter and said rigid stabilizer are configured to have a variable extension difference comprising a second distance such that said needle, limiter, and stabilizer contact said skin surface in that order, wherein said second distance is determined based upon a sharpness of said needle and said diameter of said limiter,
   wherein said limiter comprises a body and an outer face, said needle extends axially from said outer face, said body of said limiter is substantially cylindrical, and said diameter of said limiter is approximately twice an outside diameter of said needle.

2. An injectable substance delivery device as claimed in claim 1, wherein said diameter of said limiter is approximately 0.040 inches.

3. An injectable substance delivery device as claimed in claim 1, wherein:
   said needle is extended beyond said limiter along an axial direction; and said limiter is extended beyond said stabilizer by said second distance along an axial direction.

4. An injectable substance delivery device as claimed in claim 3, wherein said limiter extends by said second distance of between about 0.020 inches and about 0.100 inches beyond said stabilizer along an axial direction.

5. An injectable substance delivery device as claimed in claim 3, wherein said limiter extends by said second distance of about 0.040 inches beyond said stabilizer along an axial direction.

6. An injectable substance delivery device as claimed in claim 1, wherein said stabilizer comprises a continuous ring member concentrically located about said limiter at said first distance of approximately 0.105 inches.

7. An injectable substance delivery device as claimed in claim 6, wherein said ring member comprises an inner diameter of between about 0.10 inches and about 1.00 inches.

8. An injectable substance delivery device as claimed in claim 6, wherein said ring member comprises an inner diameter of about 0.25 inches.

9. An injectable substance delivery device as claimed in claim 1, wherein said needle comprises a needle between 31 gauge and 34 gauge.

10. An injectable substance delivery device as claimed in claim 1, wherein said needle comprises a single angle 28 degree, EDM bevel, 31 gauge needle.

11. An injectable substance delivery device as claimed in claim 1, wherein said needle comprises a single angle 28 degree, EDM bevel, 34 gauge needle.

12. An injectable substance delivery device as claimed in claim 1, wherein said needle comprises a three angle, ground bevel, 31 gauge needle.

13. An injectable substance delivery device as claimed in claim 1, wherein said needle comprises a needle having a length sufficient to penetrate said skin surface to a depth between about 0.5 mm and about 1.5 mm.

14. An injectable substance delivery device as claimed in claim 1, wherein:
said needle comprises a needle constructed of at least one of stainless steel, tungsten steel, silicon, ceramics, glass polymers, non-reactive metals, and alloys of nickel, molybdenum, chromium, cobalt and titanium; and
said limiter and said rigid stabilizer are comprised of at least one of an injection molded polymer, polycarbonate, COC polymer, polyethylene, polypropylene, polyesters, and polyamides.

15. An injectable substance delivery device comprising:
at least one needle having a length sufficient to penetrate a skin surface of a patient to an intradermal depth for infusing a substance;
a limiter pre-loaded toward said skin surface for controlling a needle insertion depth, wherein said limiter controls a maximum insertion depth of said needle into said skin surface without restricting complete insertion of said needle;
a needle holder comprising an adhesive for securing said device to said skin surface and providing an enclosed air space about said needle, wherein said needle holder is flexibly coupled to said limiter at a first distance for preventing distortion, compression, or thinning of tissue in a vicinity of a needle insertion site such that said needle length and said limiter determine the depth at which said infusion is delivered, wherein said needle holder further comprises a concave opening; and
a vacuum fitting for providing an enclosed vacuum space about said needle.

* * * * *

UNITED STATES PATENT AND TRADEMARK OFFICE
CERTIFICATE OF CORRECTION

| | |
|---|---|
| PATENT NO. | : 8,419,684 B2 |
| APPLICATION NO. | : 12/955554 |
| DATED | : April 16, 2013 |
| INVENTOR(S) | : Richard P. Clarke et al. |

Page 1 of 1

It is certified that error appears in the above-identified patent and that said Letters Patent is hereby corrected as shown below:

On the Title Page, Item (75)

The spelling of the second inventor's name is corrected from "M. Lehag Haider" to --M. Ishaq Haider--.

Signed and Sealed this
Twenty-fifth Day of June, 2013

Teresa Stanek Rea
*Acting Director of the United States Patent and Trademark Office*